United States Patent [19]

Sloviter

[11] Patent Number: 4,497,829

[45] Date of Patent: Feb. 5, 1985

[54] PROCESS FOR PREPARING PERFLUOROCHEMICAL EMULSION ARTIFICIAL BLOOD

[75] Inventor: Henry A. Sloviter, Philadelphia, Pa.

[73] Assignee: The University of Pennsylvania, Philadelphia, Pa.

[21] Appl. No.: 524,793

[22] Filed: Aug. 19, 1983

Related U.S. Application Data

[62] Division of Ser. No. 402,451, Jul. 27, 1982, Pat. No. 4,423,077.

[51] Int. Cl.³ .................... A61K 31/13; A61K 31/02
[52] U.S. Cl. ................................... 514/672; 514/756; 514/743; 514/832
[58] Field of Search .............. 424/350, 352, 365, 325

[56] References Cited

U.S. PATENT DOCUMENTS 3,958,014 5/1976 Watanabe et al.
3,962,439 6/1976 Yokoyama et al.
4,105,798 8/1978 Moore et al.
4,133,874 1/1979 Miller et al.
4,252,827 2/1981 Yokoyama et al.

OTHER PUBLICATIONS

Green Cross Corporation, "Technical Information Ser. No. 1", Dated May 15, 1975, pp. 38-39.

Primary Examiner—Sam Rosen
Attorney, Agent, or Firm—Seidel, Gonda & Goldhammer

[57] ABSTRACT

Particles of perfluoro compound with a lipid coating are emulsified by sonification in aqueous medium, wherein the proportion of perfluoro compound in the emulsion is preferably about 30-75% (w/v) and the proportion of lipid is preferably about 7-9% (w/v). In the resulting stable emulsion 95% of these particles having diameters less than $0.2\mu$. The emulsion is useful as an artificial blood for transport and delivery of oxygen to body tissues.

12 Claims, No Drawings

PROCESS FOR PREPARING PERFLUOROCHEMICAL EMULSION ARTIFICIAL BLOOD

This application is a divisional of my co-pending applicaton Ser. No. 402,451, filed July 27, 1982, now U.S. Pat. No. 4,423,077 for "PERFLUOROCHEMICAL EMULSION ARTIFICIAL BLOOD".

BACKGROUND OF THE INVENTION

The present invention is directed to a perfluorochemical emulsion which is useful as an artificial blood for the transport of oxygen.

Natural whole blood is in short supply, and the shortage will probably increase. New methods for prolonged preservation of blood in the frozen state and improvements in storage in the liquid state have resulted in more efficient use of available blood in some areas, but the world-wide need for blood for transfusion still far exceeds the supply. Since it is unlikely that there will be any appreciable increase in supply, needs must be satisfied by substances other than natural blood or its derivatives. An artificial blood, available in unlimited quantities and free from infectious agents and antigens, would be an extremely valuable therapeutic agent.

Emulsions of perfluoro compounds now seem likely to be successful as artificial blood. Perfluorochemical emulsion artificial bloods are free of infectious agents and antigens. (hereinafter, perfluoro compound and perfluorochemical shall be used interchangeably.) Blood typing of the recipient is unnecessary. However, such artificial bloods lack clotting factors, platelets, immunoglobulins, and antibodies.

Perfluorochemical emulsions have been used successfully as substitutes for red blood cells in perfusing isolated animal organs and in the delivery of oxygen to the tissues of intact animals. Recently, an emulsion of perfluorochemicals was used in treating human subjects.

Although perfluoro compounds are chemically inert, they may adversely affect blood platelets and blood coagulation factors, resulting in thrombocytopenia (i.e., decrease in the absolute number of blood platelets) and disorders of blood coagulation. It has been found that the effects on platelets are likely due to unusual surface properties of perfluoro compounds, namely a very low surface tension. This effect can be overcome by coating the perfluoro compound particles with a substance which masks its surface activity.

The efficacy of perfluorochemical emulsions as artificial bloods is limited by the relatively short retention time of the emulsion particles in circulation. It would therefore be desirable to provide emulsion particles which have an extended duration in circulation and do not affect platelet aggregation or clotting factors.

Artificial blood compositions comprising perfluorochemicals in phospholipid emulsifiers are known in the art. However, such prior art emulsions contain substantially less perfluorochemical, and substantially less emulsifier, than the present invention. They are also substantially less stable.

U.S. Pat. No. 3,958,014 discloses the preparation of a perfluorocarbon emulsion in lecithin. The preferred concentrations of perfluorocarbon and lecithin are 25–30% (w/v) and 3–5% (w/v), respectively. (Hereinafter, "% (w/v)" shall mean the amount of a material, measured in grams, contained in 100 ml of emulsion; "%(v/v)" shall mean the volume of a material measured in ml, contained in 100 ml of emulsion.)

U.S. Pat. No. 3,962,439 teaches perfluorochemical emulsions in lecithin containing 10–40% (w/v) perfluorocarbon and 2–6% (w/v) lecithin. The emulsions of this patent are unstable.

"FLUOSOL-DC" is an emulsion prepared by Green Cross Corporation (see brochure dated May 15, 1975 "Technical Information Ser. No. 1", p. 38-39). "FLUOSOL-DC" must be stabilized by pasteurizatin at 60° C. for one hour on three successive days since heat sterilization at 100° C. destroys the emulsion. It must be sterilized under relatively mild conditions—repeated heating at 60° C. Within six hours after infusion into the recipient, the phospholipid layer surrounding the perfluorocarbon particle decays. The nude perfluoro particles then disappear from the circulation.

U.S. Pat. No. 4,105,798 teaches a perfluorochemical emulsion in lecithin containing 10–30% (v/v) perfluorocarbon and 1–5% (v/v) lecithin.

It was recently discovered that an emulsion of improved stability results from the combination of two perfluorochemical compounds. The emulsion which is the subject of U.S. Pat. No. 4,252,827 is an emulsion of two perfluorocarbons (10–50% w/v total), in a high molecular weight nonionic surfactant emulsifier (2.0–5.0% w/v), a phospholipid "emulsifier adjuvant" (0.1–1.0% w/v), and a fatty acid (0.004–0.1% w/v). This composition, although more stable than other compositions, is of limited utility. It is prepared and stored in three separate components which must be kept frozen until just prior to the time of infusion. Infusion must occur within 24 hours of thawing and mixing. Thawing results in loss of emulsion stability. Most significantly, this emulsion cannot be autoclaved by conventional techniques. Sterilization is carried out at 115° C. for 12 minutes in a specially designed rotary sterilizer. Emulsions of U.S. Pat. No. 4,252,827 are isotonic, but hyperionic.

"PLURONIC F-68", a high molecular weight nonionic surfactant, is the emulsifier used in "FLUOSOL-DA", a composition prepared according to U.S. Pat. No. 4,252,827 which is a product of Green Cross Corporation of Japan. Investigators have found that "PLURONIC F-68" inhibits blood coagulation and aggregation of platelets.

SUMMARY OF THE INVENTION

An artificial blood composition is provided containing oxygen-transporting perfluorochemical particles emulsified in a physiologically acceptable aqueous medium, the perfluorochemical particles being coated with a lipid which is non-antigenic. The proportion of perfluoro compound in the emulsion is preferably about 15–40% (v/v), corresponding to about 30–75% (w/v). The proportion of lipid in the emulsion is preferably about 7–9% (w/v). This is substantially higher than prior art perfluorochemical emulsions. Various physiologically acceptable salts may also be contained in the emulsion.

Perfluorodecalin is the preferred perfluoro compound. A preferred lipid is a phospholipid such as lecithin, available in the form of egg yolk phospholipid. Lecithin is also present in soybean phospholipid.

The perfluoro compound emulsion of the present invention is prepared by addition of perfluoro compound to the lipid dispersed in an aqueous medium by sonication. The mixture is sonicated further and centrifuged. Large particles are eliminated by discarding the bottom fraction of the emulsion.

The present invention is the first stable emulsion of a single perfluorochemical useful as an artificial blood which is nonhemolytic, autoclavable by conventional techniques, and storable at normal refrigeration temperatures. The composition may even be stored at room temperatures for considerable periods. Finally, the present composition is both isotonic and isoionic with respect to natural blood plasma.

DETAILED DESCRIPTION OF THE INVENTION

An emulsion of perfluoro compounds of increased stability results from the present invention. The emulsion preferably contains about 15-40% (v/v) perfluoro compound, corresponding to about 30-75% (w/v). The emulsion preferably contains about 7-9% (w/v) lipid which may act as both coating agent and emulsifier. The preferred perfluoro compound is perfluorodecalin. The preferred lipid is lecithin.

The concentration of perfluoro compound may depart slightly from these limits. However, emulsions containing substantially greater than 75% (w/v) perfluoro compound will be too viscous to be useful as artificial blood. Emulsions containing substantially less than 15% (w/v) perfluoro compound will be so dilute that too much emulsion will be required to provide good oxygen transport.

Perfluorochemicals have the ability to take up and release oxygen. However, the use of perfluorochemicals in artificial blood preparations is limited to a large extent by the effect of perfluorochemicals on platelets. This effect is overcome by coating the perfluoro compound particles with a coating material which masks the surface activity of the perfluorochemical while imitating the outward appearance (to the circulatory system) of a normal red blood cell.

The present invention makes use of lipid to coat particles of perfluorochemicals. The preferred lipids are phospholipids such as lecithin. The coated particles are contained in an emulsion. The emulsifier may be the same substance which coats the particles, i.e. phospholipid, or it may be a different substance. Lecithin has the advantage that it is itself an acceptable emulsifier; hence additional emulsifiers are not necessary.

Not all perfluorochemicals are useful in artificial blood preparations. Perfluorochemicals tend to accumulate in body tissues, notably the liver and spleen. Some perfluorochemicals are emulsified only with difficulty. Perfluorodecalin has been found to be the best perfluorochemical in terms of speed of elimination from the liver and spleen. Perfluorotripropylamine is more easily emulsified than perfluorodecalin but has a considerably slower rate of elimination from the liver and spleen. Other perfluoro compounds which have been used are perfluoromethyldecalin and perfluorotributylamine. Emulsions of perfluorobutyltetrahydrofuran have been found unacceptable as artificial bloods.

According to the invention, perfluorochemical particles are coated with an adherent lipid which will not be rejected by the recipient but will appear to the circulation as the membrane of a natural red blood cell. It has been found that phospholipid is acceptable, with egg yolk phospholipid, or lecithin, being preferred. Lecithin, being a component of natural blood cells, not only simulates the membrane of natural erythrocytes, but is nontoxic (non-antigenic) to the recipient. Moreover, it has been found that lecithin has no effect on blood coagulation. The perferred source of lecithin is egg yolk phospholipid. Lecithin is also available in a less pure form in soybean phospholipid.

In a preferred embodiment of the invention, lipid is used both as a particle coating and an emulsifier, thereby dispensing with the need for an additional emulsifier. However, if desired, an acceptable emulsifier may be used, for example, one of the nonionic surfactants, such as are available commercially under the trademark "PLURONIC" from BASF-Wyandotte Corp.

In the preferred embodiment, the perfluoro particles are coated with adherent lecithin in the amount of about 50-70 $\mu$mols/ml of perfluorochemical. The increased concentration of lecithin (7-9% (w/y)) results in a substantially more stable lecithin-coated emulsion particle, remaining in the circulation up to four days. Prior art lecithin-coated perfluoro particles such as "FLUOSOL-DC" (3.6% (w/v)) remain stable in circulation for only about six hours.

Particles larger than natural erythrocytes, which are about 7-10$\mu$ in diameter will not pass through small capillaries. Moreover, large particles are removed from the circulatin more quickly than smaller ones. Particles greater than 0.6$\mu$ are believed toxic. The optimum particle size is about 0.1$\mu$.

The emulsion particles of the present invention are on the average about 0.1$\mu$ in diameter. Preferred artificial bloods of the present invention, upon examination by dark-field microscopy exhibited more than 95% of the particles with diameters below 0.2$\mu$. In dark-field microscopy, particles 0.2$\mu$ and larger are visible as discrete structures; particles less than 0.2$\mu$ in diameter are not visible but give rise to diffuse illumination of the field.

Emulsions of the present invention are prepared in physiologically acceptable aqueous media. The medium should contain the necessary electrolytes at the proper concentrations to make the emulsion both isotonic and isoionic with respect to blood plasma. Prior art artificial blood emulsions are hyperionic and therefore less stable in blood plasma.

It has been found that Tyrode solution is an acceptable medium. Tyrode solution is an aqueous solution containing the following: NaCl, KCl, CaCl$_2$, MgCl$_2$, NaH$_2$PO$_4$, NaHCO$_3$ and glucose. Electrolyte concentrations should be selected to render the resulting emulsion isotonic and isoionic with respect to blood plasma.

The pH of the resulting emulsion is adjusted to between 7.2 and 7.6. An emulsion pH of 7.4, the pH of blood plasma, is optimal. The osmotic pressure is ideally 300mOsm/l. The electrolytes and respective electrolyte concentrations of a preferred embodiment are listed in Table 1.

TABLE 1

| Electrolyte | Electrolyte Concentration (Percent w/v) |
|---|---|
| NaCl | 0.75 |
| KCl | 0.015 |
| CaCl$_2$ | 0.02 |
| MgCl$_2$ | 0.007 |
| NaH$_2$PO$_4$ | 0.004 |
| NaHCO$_3$ | 0.07 |
| Glucose | 0.07 |

Artificial blood emulsions of the present invention are prepared by adding a perfluoro compound to dispersed lipid in a physiologically acceptable aqueous medium, followed by sonication and centrifugation. This process differs markedly from prior art procedures which rely on mechanical homogenization. The process of the present invention is described as follows:

Purified lipid is dispersed in a physiologically acceptable medium of approximately pH 7.4 Sonication is preferred over mechanical homogenization. Sonication may be repeated after a brief interval to ensure adequate dispersion. An amount of perfluoro compound is then added, followed by repeated sonication at low temperature until a milky-white emulsion forms. The amount of perfluoro compound added may be varied in accordance with the perfluoro compound concentration desired in the final emulsion.

Large particles are removed from the resulting emulsion by extended low-speed, low-temperature centrifugation. Since perfluorochemicals are relatively dense (1.9-2.0 specific gravity) low-speed centrifugation is satisfactory. Centrifugation at 0° C. and $100 \times g$ has been used. The bottom fraction of the emulsion, which contains particles large enough to be toxic, is discarded.

After 20 weeks storage at 4° C., particles were reexamined under dark-field microscopy. No change in particle size was observed. Moreover, upon centrifugation after storage, no change in the sedimentation rate was observed. The absence of any change in particle size or sedimentation rate indicates the continued stability of the particles.

The present emulsion may be sterilized by conventional hospital autoclave procedures at temperatures above 120° C. at a steam pressure of 15 lb/in.$^2$ without phase separation or change in particle size. Moreover, the present emulsion may be autoclaved before storage and taken out of storage for immediate use without further autoclaving. This is a significant advance over prior art perfluro compound emulsions which require further mixing of solutions before the composition may be used after storage.

The present invention will be illustrated in more detail by reference to the following non-limiting examples:

EXAMPLE 1

Preparation of Perfluoro Compound Emulsion

To 7 ml of cold Tyrode solution (pH 7.4)in a Rosette cell was added 960 mg of purified lecithin (derived from egg yolks). The mixture was sonicated at 110 watts for 15 sec. Sonication was repeated once after an interval of 1 min. To this dispersed lecithin in a Rosette cell at 0° C., was added 4 ml of perfluoro compound (perfluorotripropylamine or perfluorodecalin), and the mixture was sonicated as before for eight 15 sec. periods with an interval of 1 minute after each sonication. The resulting milky white emulsion was centrifuged at 4° C. for 60 minutes at 100 x g to sediment any large particles. The bottom 5% of the emulsion was discarded. The emulsion contained 35-40% (v/v) [67-76% (w/v)] dispersed perfluoro compound, and its pH was between 7.35 and 7.40. The emulsifed perfluoro particles were about 0.1 $\mu$m in diameter and contained 50-70 $\mu$mols of lecithin per ml of perfluoro compound (about 7-9% (w/v) of the emulsion).

The lecithin content of the perfluoro particles was measured by twice washing the sedimented particles from an aliquot of the emulsion with Tyrode solution, extracting the lecithin with a mixture of chloroform and methanol, and determining the phosphorus content of the extract. The amount of lecithin present, measured in micromoles, is calculated by (1) dividing the phosphorous content in micrograms by a factor of 31 (the atomic weight of phosphorus). This calculation yields the micromoles of lecithin since one molecule of lecithin contains one phosphorus atom.

The preparation set forth in Example 1, which makes use of ultrasonic emulsification, differs markedly from the prior art processes for producing perfluorocarbon emulsions which utilize mechanical homogenizers.

The perfluorodecalin and perfluorotripropylamine emulsions prepared according to Example 1 were administered to two separate groups of laboratory rats as described in Example 2.

EXAMPLE 2

Infusion of Perfluoro Compound Emulsion Into Rats

Male Sprague-Dawley rats (200-250 g) anesthetized with pentobarbital (30 mg/kg) received 8 to 10 ml. of emulsion per rat infused by a pump into the femoral vein at 0.2 ml/min. An approximately equal volume of blood was withdrawn during the infusion. Blood samples were obtained at intervals after infusion for measurement of hematocrit, concentration of perfluoro compound, and platelet count. The concentration of perfluoro compound in the blood of rats at completion of infusion was in the range of 19-22% (v/v). In one group of rats these values were in the range of 24-28% (v/v).

All rats infused with emulsions of perfluorodecalin (more than 100 rats) or emulsions of perfluorotripropylamine (more than 100 rats) have remained in good health for more than one year. The platelet counts of the blood of these rats did not change significantly after the infusion of either of these emulsions; this is in contrast to the decrease in blood platelets observed after infusion of most other perfluoro compound emulsions.

The present invention may be embodied in other specific forms without departing from the spirit or essential attributes thereof and, accordingly, reference should be made to the appended claims, rather than to the foregoing specification, as indicating the scope of the invention.

I claim:

1. A process for preparing a stable emulsion comprising:
   (a) dispersing purified lipid in a physiologically acceptable aqueous medium by sonication;
   (b) adding perfluoro compound to the dispersion formed in (a);
   (c) sonicating the mixture of lipid and perfluoro compound formed in (b) to form an emulsion of lipid-coated particles of perfluoro compound; and
   (d) centrifuging the emulsion formed in (c) to separate oversize particles.

2. A process according to claim 1 wherein the perfluoro compound is selected from the group consisting of perfluorodecalin, perfluoromethyldecalin, perfluorotripropylamine and perfluorotributylamine.

3. A process according to claim 2 wherein the lipid is lecithin.

4. A process according to claim 2 wherein the perfluoro compound is perfluorodecalin.

5. A process according to claim 2 wherein the perfluoro compound is perfluorotripropylamine.

6. A stable emulsion prepared according to claim 1.
7. A stable emulsion prepared according to claim 2.
8. A stable emulsion prepared according to claim 3.
9. A stable emulsion prepared according to claim 4.
10. A stable emulsion prepared according to claim 5.
11. A process for preparing a stable emulsion comprising:
   (a) dispersing purified lecithin in cold Tyrode solution (pH 7.4) by sonication;
   (b) repeating the sonication of said lecithin;
   (c) forming an emulsion by adding to said dispersed lecithin a perfluoro compound and sonicating the mixture, repeating said sonication with an interval between each sonication;
   (d) centrifuging said emulsion; and
   (e) discarding a bottom fraction of said emulsion.
12. A stable emulsion prepared according to claim 11.

* * * * *